US008401204B2

(12) United States Patent
Odent et al.

(10) Patent No.: US 8,401,204 B2
(45) Date of Patent: Mar. 19, 2013

(54) METHOD FOR THE ACTIVE REDUCTION OF SOUND DISTURBANCE

(75) Inventors: Jean-Claude Odent, Lattes (FR); Benoît Mazeaud, Lyons (FR)

(73) Assignee: Quietys, Montpellier (FR)

( * ) Notice: Subject to any disclaimer, the term of this patent is extended or adjusted under 35 U.S.C. 154(b) by 861 days.

(21) Appl. No.: 12/530,506

(22) PCT Filed: Mar. 4, 2008

(86) PCT No.: PCT/FR2008/050371

§ 371 (c)(1), (2), (4) Date: Sep. 9, 2009

(87) PCT Pub. No.: WO2008/125774

PCT Pub. Date: Oct. 23, 2008

(65) Prior Publication Data

US 2010/0034398 A1 Feb. 11, 2010

(30) Foreign Application Priority Data

Mar. 9, 2007 (FR) ..................................... 07 01718

(51) Int. Cl.
*A61F 11/06* (2006.01)

(52) U.S. Cl. ................. 381/71.11; 381/71.12; 381/71.3; 381/71.4; 381/71.8

(58) Field of Classification Search ............... 381/71.11, 381/71.12, 71.3, 71.4, 71.8

See application file for complete search history.

(56) References Cited

U.S. PATENT DOCUMENTS

| | | | | |
|---|---|---|---|---|
| 5,940,519 | A | 8/1999 | Kuo | |
| 5,978,489 | A * | 11/1999 | Wan | 381/71.11 |
| 2002/0003887 | A1 | 1/2002 | Zhang et al. | |
| 2004/0234080 | A1 | 11/2004 | Hernandez | |

FOREIGN PATENT DOCUMENTS

| | | |
|---|---|---|
| WO | 03015074 | 2/2003 |
| WO | 03088207 | 10/2003 |
| WO | 03088207 A1 | 10/2003 |

OTHER PUBLICATIONS

French Search Report mailed Nov. 7, 2007, 2 pages.

International Search Report mailed Nov. 20, 2008 in corresponding PCT/FR2008/050371, 3 pages.

International search report dated Nov. 20, 2008 in corresponding PCT/FR2008/050371.

* cited by examiner

*Primary Examiner* — Vivian Chin
*Assistant Examiner* — Paul Kim
(74) *Attorney, Agent, or Firm* — Young & Thompson

(57) ABSTRACT

A method and a system for the active reduction, at a predetermined area, of the energy of a sound signal ($d_k(n)$), also called a diffused noise signal, generated at the area by a primary signal ($x_k(n)$), or noise signal, by the emission of a plurality of counter-noise signals ($y_k(n)$) having an effect antagonistic to the diffused noise signal ($d_k(n)$), each of the counter-noise signals ($y_k(n)$) including a feedback counter-noise signal ($yfbk_k(n)$) and a feed-forward counter-noise signal ($yfwd_k(n)$). The method includes detecting the periodical components of diffused noise signal ($d_k(n)$) for adjusting the feedback counter-noise signal ($yfbk_k(n)$), and modelling the inverse of the secondary path for adjusting the feedback counter-noise ($yfbk_k(n)$) and feed-forward counter-noise ($yfwd_k(n)$) signals. The invention can be implemented to any type of industrial or non-industrial noise and in any location such as working places and relaxation places.

17 Claims, 6 Drawing Sheets

METHOD FOR THE ACTIVE REDUCTION OF SOUND DISTURBANCE

The present invention relates to a method of reducing noise disturbances by active control. It also concerns a system implementing the method according to the invention.

The invention aims, in particular, to reduce noise disturbances in a determined zone by an active reduction method. Noise disturbances can be any types of annoying acoustic waves which can be considered noise in a determined zone. These disturbances can be of all types and of frequencies which can range from a few hertz to a few thousand hertz. They can be created by any working device. In the case, for example, of a sealed enclosure, the disturbances can be generated by devices which are situated inside this enclosure. They can also be caused by sources outside the enclosure when the latter is, for example, situated close to sites such as an airport, a motorway, a railway line etc.

Current systems for the active reduction of noise disturbances make it possible to attenuate these disturbances by two types of methods. The first, called feedforward, requires prior information on the noise signal which is the cause of the noise disturbance to be reduced. The detection of the noise signal is carried out upstream of the processing zone by active reduction and delivers a reference signal which must be closely correlated with the noise disturbance to be reduced. In this case, the prior knowledge of the noise signal is used to minimize the noise disturbance reduction error, this error being quantified by a so-called error signal measured in the determined zone. However, the prior information on a noise disturbance is not always available, hence the use of a second noise disturbances reduction method, called feedback, or closed-loop control, in which no prior detection is carried out. The reduction error signal is used to provide a control signal intended to minimize this same error signal.

However, most of the current systems provide solutions limited to the causality constraint indispensable for the satisfactory implementation of certain active control applications. This makes it necessary to carry out the digital operations intrinsic to the active reduction method in a very short time. Therefore, these systems have limited effectiveness in terms of reaction time, in space and in terms of frequency.

An objective of the invention is thus to propose a method for the active reduction of noise disturbances making it possible to better satisfy the abovementioned constraint, and therefore to achieve a better reduction of the noise disturbances.

The invention proposes to remedy the abovementioned problem by a method for the active reduction in a determined zone of the energy of a sound signal, called propagated noise signal, generated in the determined zone by a primary signal, called noise signal. The method comprises a transmission, by transmission means, of at least one counter-noise signal comprising at least a first counter-noise signal, called feedback, counteracting the propagated noise signal, this method also comprising at least one iteration of the following operations:

- measurement, by measurement means arranged in the determined zone, of a so-called error signal, representing information on the effectiveness of the reduction of the energy of the propagated noise signal in the zone;
- modelling, by at least a first filter, of a direct acoustic path, called secondary path, between the means for transmitting the counter-noise signal and the means of measuring the error signal optionally during a prior identification step;
- detection of at least one periodic component of the propagated noise signal by filtering of said propagated noise signal, said detection providing said periodic component; and
- adjustment of the feedback counter-noise signal as a function of the detected periodic component, the error signal and the modelled secondary path.

In the present application, the sources of the counter-noise signal are called the secondary sources and the sources of the noise signal the primary sources.

The measurement of the error signal, by a measurement means constituted for example by a monitoring microphone, makes it possible to record the reduction of the energy of the propagated noise signal and to adjust the counter-noise signal so as to reduce this same error signal.

The modelling of the secondary path can be carried out by transmission, by a counter-noise signal transmission means constituted for example by a speaker, of a known signal, followed by a measurement of this signal in the determined zone by a measurement means. Thus, knowing the transmitted signal and the measured signal, it is possible to characterize the acoustic path between the counter-noise signal transmission means and the measurement means in the determined zone. This modelling can take place before or during any counter-noise transmission phase.

Once this path has been determined, and still before any reduction in the noise signal, a modelling of the inverse of the secondary path can be carried out digitally so as not to introduce phase shift i.e. additional delay in the control chain, which would be contrary to the main objective of the invention. A modelling of the amplitude alone is consequently carried out. This inverse filter makes it possible to limit the resonances inherent in the electro-acoustic equipment used and in the topography of the processing zone, resonances that are found in said secondary path.

What follows occurs during the actual control phase.

The detection of the periodic components of the propagated noise signal allows better knowledge of the spectral composition of said signal and consequently makes it possible to carry out band-pass filtering operations. The counter-noise signal can thus be adjusted optimally in order to ensure, in greater stability, the better reduction of the energy of the propagated noise signal and therefore of the nuisance caused by the noise signal in the determined zone, in particular during rapid changes of the periodic components.

The propagated noise signal can be estimated on the one hand from the error signal and on the other hand from the feedback counter-noise signal processed by the first filter modelling the secondary path. In fact, by subtracting from the error signal measured in the determined zone the feedback counter-noise signal filtered by the first filter modelling the secondary path, i.e. the acoustic path between the secondary source and the measurement means in the determined zone, it is possible to carry out an estimation of the propagated noise signal to be reduced.

The detection of the periodic components of the propagated noise signal can be carried out by a filtering of the estimated propagated noise signal by "notch" type band-pass filters, for cutting, carrying out an infinite impulsional response (IIR) band-pass filtering of constant amplitude everywhere except at the frequencies of the periodic components of the propagated noise signal where the pass bands are virtually zero. These filters are called adaptive notch filters (ANF).

Moreover, the method according to the invention comprises a band-pass filtering of the estimated propagated noise signal, at the frequency of all or some of the detected periodic components, said filtering providing a so-called reference signal, essentially constituted by the periodic components of the propagated noise signal. This reference signal is then used in the adjustment of the feedback counter-noise signal, as described below.

In fact, the method according to the invention comprises an adjustment of at least one coefficient of a second, finite impulsional response, filter provided in order to adjust the feedback counter-noise signal according to the reference signal filtered by a third, finite impulsional response, filter amplitude modelling the inverse of the secondary path. The filtered reference signal thus obtained, composed essentially of the periodic components of the estimated propagated noise signal, therefore serves as a basis for the adjustment of the coefficients of the second filter, the role of which is precisely to eliminate the periodic components of the propagated noise signal. The filtering operation, by the third filter modelling by amplitude the inverse of the secondary path, makes it possible to facilitate the adjustment of the coefficients of the second filter.

In fact, the result, at the output, of combining on the one hand the first filter modelling the secondary path and on the other hand the third filter amplitude modelling the inverse of the secondary path is a flat amplitude response, equal to 1. This facilitates the work of the second filter which is to find the optimum amplitudes and phases of the feedback counter-noise signal which minimize the energy of the error signal and therefore the energy of the propagated noise signal. In fact, ensuring this unit amplitude makes it possible to free the second filter from the task of seeking optimum amplitude and concentrate solely on seeking the optimum phase.

Advantageously, at least one coefficient of the second filter can be adjusted by an algorithm of the minimization algorithm type according to the least mean squares (LMS) criterion as a function of the reference signal processed by the first filter, the error signal that has undergone a band-pass filtering at the frequency of all or some of the detected periodic components and a so-called feedback convergence coefficient that plays a part in the LMS algorithm. By carrying out such band-pass filtering on the error signal, it is thus possible to isolate the periodic components of the propagated noise signal which are present in the error signal in order that the second filter concentrates only on these.

Advantageously, the counter-noise signal also comprises a so-called feedforward counter-noise signal, adjusted as a function of the error signal and the noise signal measured by measurement means comprising for example a microphone. The feedforward counter-noise signal is intended to reduce the energy of the non-periodic components of the noise signal. Thus, the method according to the invention makes it possible to use a combination of a feedback counter-noise signal and a feedforward counter-noise signal intended respectively to reduce the energy of the periodic components and the non-periodic components of the noise signal.

Moreover, the method according to the invention can also comprise:

- an amplitude modelling of the inverse of the secondary path by at least a fourth, finite impulsional response, filter and
- a modelling by at least a sixth, finite impulsional response, filter of the secondary path, still with a view to facilitating the task of adjusting the coefficients of a fifth filter defined hereafter. The fourth filter can be identical to the third filter and the sixth filter identical to the first filter. In a non-limitative embodiment example, the fourth filter can be the third filter and the sixth filter can be the first filter.

The adjustment of the feedforward counter-noise signal comprises an adjustment of a fifth, finite impulsional response, filter provided to adjust said feedforward counter-noise signal as a function of the noise signal processed beforehand by the fourth filter.

Moreover, at least one coefficient of the fifth filter is adjusted by an algorithm of the minimization algorithm type according to the least squares criterion as a function of the error signal, the noise signal measured and processed beforehand by the sixth filter modelling the secondary path and a so-called feedforward convergence coefficient that affects the algorithm in question.

As previously, the result, at the output, of combining on the one hand the fourth filter modelling the secondary path and on the other hand the sixth filter amplitude modelling the inverse of the secondary path is a flat amplitude response, equal to 1.

Advantageously, the method according to the invention can be used to attenuate at least one noise signal by transmission of a plurality of counter-noise signals by a plurality of transmission means. Each of the counter-noise signals can comprise:

- a feedback counter-noise signal,
- a feedforward counter-noise signal, or
- a feedback counter-noise signal and a feedforward counter-noise signal.

Through the transmission of a plurality of counter-noise signals, and the use of a plurality of points measuring error signals, for example monitoring microphones, the method according to the invention makes it possible on the one hand to increase the size of the determined zone in which it is sought to carry out a reduction of the energy of at least one propagated noise signal, and on the other hand to carry out this reduction up to higher frequencies. Thus, by increasing the number of pairs of counter-noise signal transmission means/error signal measurement means, in other words counter-noise signal/error signal, it is possible to process noise disturbances over a greater distance and in a wider frequency band.

For example, the method according to the invention can be used to produce an “acoustic comfort bubble”. As the spatial extent of such an acoustic comfort bubble in free space is fairly confined as the frequency increases, several sources of transmission of several counter-noise signals and several microphones monitoring the reduction of the energy of the propagated noise signal must be envisaged. For example, knowing that the space between the ears is approximately 20 centimeters, and that an identical margin is taken in order to allow a user complete freedom to reasonably move his head, the acoustic comfort bubble to be produced will be 40 centimeters in diameter, i.e. effective processing up to 200 Hz maximum considering only a single pair of counter-noise signal transmission means/error signal measurement means. By multiplying the disturbances reduction points, i.e. the number of monitoring microphones, it is possible to increase the maximum frequency of the noise signals of which it is desired to reduce the energy. Thus, with 3 noise disturbances reduction points over this distance, it is possible to process noise signals up to approximately 700 Hz in a comfort bubble 40 cm in diameter. By multiplying the number of counter-noise signals and the number of reduction points and arranging them appropriately, it is also possible to increase the size of the comfort bubble.

By reduction, or minimization, point is meant the location of a monitoring microphone provided to measure an error signal.

According to another feature of the invention, a system is proposed for the active reduction, in a determined zone, of the energy of a sound signal, called propagated noise signal, generated in the determined zone by a primary signal, called noise signal, by transmission of at least one counter-noise signal comprising at least a first so-called feedback counter-noise signal, counteracting the propagated noise signal in the determined zone, the system comprising:

means for transmitting the counter-noise signal;

means for measuring, in the determined zone, a so-called error signal, representing information on the effectiveness of the reduction of the energy of the propagated noise signal;

at least one first filter for modelling a direct acoustic path, called secondary path, between the means for transmitting the counter-noise signal and the means of measuring the error signal optionally obtained at the end of a prior identification step;

means for detecting and providing at least one periodic component of the propagated noise signal; and means for adjusting the feedback counter-noise signal as a function of the detected periodic component, the error signal and the modelled secondary path.

Advantageously, the means for transmitting the counter-noise signal can comprise directional ultrasonic transducers having a reduced transmission beam. In fact, one of the limitations of the current systems of active reduction of a noise disturbance is that, although the counter-noise contributes to a reduction in the noise signal in a targeted zone or volume, it is perfectly able to increase them elsewhere. In other words, reducing the disturbances in a space does not mean reducing them throughout the whole space. Furthermore, means for transmitting a counter-noise signal such as speakers are more directional at low frequencies than at high frequencies. Unless it is possible to have available speakers which are larger than the largest of the wavelengths inherent in the spectrum of the noise signal to be processed, it will not be possible to escape this limitation, unless ultrasonic transducers are used. Ultrasounds, which are completely inaudible when transmitted, distort as they are propagated in the air and shift into the audible spectrum. The advantage of ultrasonic transducers is that they have a very reduced transmission beam and the volume in which the ultrasounds become audible is completely predictable. Another advantage of the use of such transducers is that their directivity simplifies the multi-route system. In fact, the transposition to the multi-route case from the single-route system involves consideration of a large number of secondary paths: the direct secondary paths between each transducer and their associated monitoring microphone, but also the so-called crossed secondary paths which represent the interactions between all the transducers and the microphones. On the other hand, the contributions of each secondary source to the means of measuring the noise signal, called back contributions, must be considered in the same way. This requires electronics with a large computational and memory capacity. To minimize the often significant costs of the real-time operations inherent in the calculation of the counter-noise signals, the directivity of the ultrasonic transducers has a great advantage in that, instead of one complex multi-route system, a parallelization of many much less complex single-route systems can be considered. In fact, in this case, the crossed paths and the back contributions become negligible due to the directivity of the ultrasonic transducers and the stability of the system is not disturbed as a result of not taking account of the entities in the parallelized structure.

The system according to the invention can moreover comprise means for measuring the noise signal. These means can comprise at least one so-called noise microphone, appropriately positioned depending on the source of noise.

The system according to the invention can moreover comprise means for estimating the propagated noise signal in the determined zone. The estimation of the propagated noise signal, as it presents itself in the determined zone, can be carried out as a function of the error signal and of the counter-noise signal.

Moreover, the system according to the invention can comprise means for band-pass filtering of the estimated propagated noise signal at the frequency of all or some of the periodic components of the propagated noise signal, and arranged in order to generate a reference signal, as described above.

The means for adjusting the feedback counter-noise signal can advantageously comprise at least a second, finite impulsional response, filter, provided to adjust said feedback counter-noise signal as a function of the reference signal filtered by a third, finite impulsional response, filter arranged for amplitude modelling the inverse of the secondary path.

Advantageously, the counter-noise signal can comprise a second so-called feedforward counter-noise signal, the system according to the invention also comprising means for transmitting the feedforward counter-noise signal adjusted as a function of the error signal and the noise signal.

The system can comprise a fourth, finite impulsional response, filter amplitude modelling the inverse of the secondary path, a fifth filter, provided to adjust the feedforward counter-noise signal, as a function of the measured noise signal processed by the fourth filter and a sixth, finite impulsional response, filter, arranged for modelling the secondary path.

The system according to the invention can advantageously comprise a plurality of means for transmitting a plurality of counter-noise signals, used to attenuate at least one noise signal.

Other advantages and characteristics of the invention will become apparent on examination of the detailed description of an embodiment which is in no way limitative, and the attached drawings in which.

Figure 1:
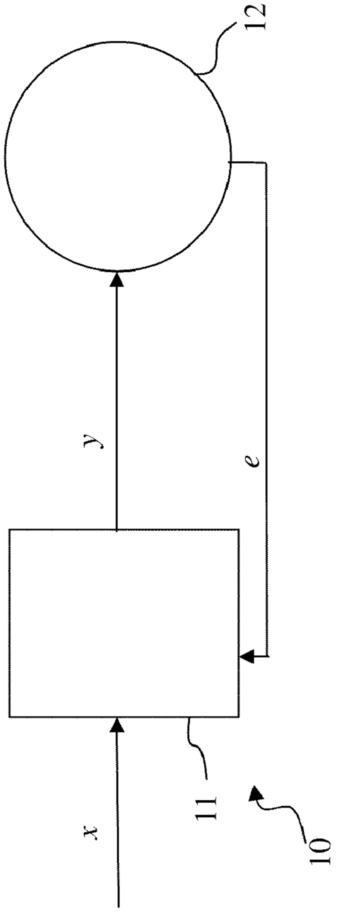
FIG. 1 is a diagrammatic representation of a configuration for the active reduction of a sound signal by means of a single-route system according to the invention.

FIG. 1 is a diagrammatic representation of a configuration 10 for the active reduction of noise disturbances by means of a single-route system 11 according to the invention. This system 11 comprises a noise microphone making it possible to measure a noise signal x and a transducer transmitting a counter-noise signal y adjusted to minimize the noise disturbances caused by the noise signal x in an acoustic comfort zone 12 where a monitoring microphone is arranged making it possible to measure an error signal e. In the remainder of the description, the acoustic comfort zone 12 thus created will be called "acoustic comfort bubble".

Now, the spatial extent of such an acoustic comfort bubble 12 in free space is fairly confined as the frequency increases, so several pairs of transducer/monitoring microphone must be envisaged. For example, knowing that the space between the ears is approximately 20 centimeters, and that an identical margin is taken in order to allow a user complete freedom to reasonably move his head, the acoustic comfort bubble to be produced must be 40 centimeters in diameter, i.e. effective processing up to 200 Hz maximum considering only a single transducer/monitoring microphone pair combination. By multiplying the number of transducer/monitoring microphone pairs, it is possible to increase the maximum processing frequency. Thus, with 3 noise disturbance reduction points over this distance, it is possible to process disturbances up to approximately 700 Hz in a comfort bubble 40 cm in diameter. By multiplying the number of counter-noise signals and the number of reduction points and arranging them appropriately, it is also possible to increase the size of the comfort bubble.

Figure 2:
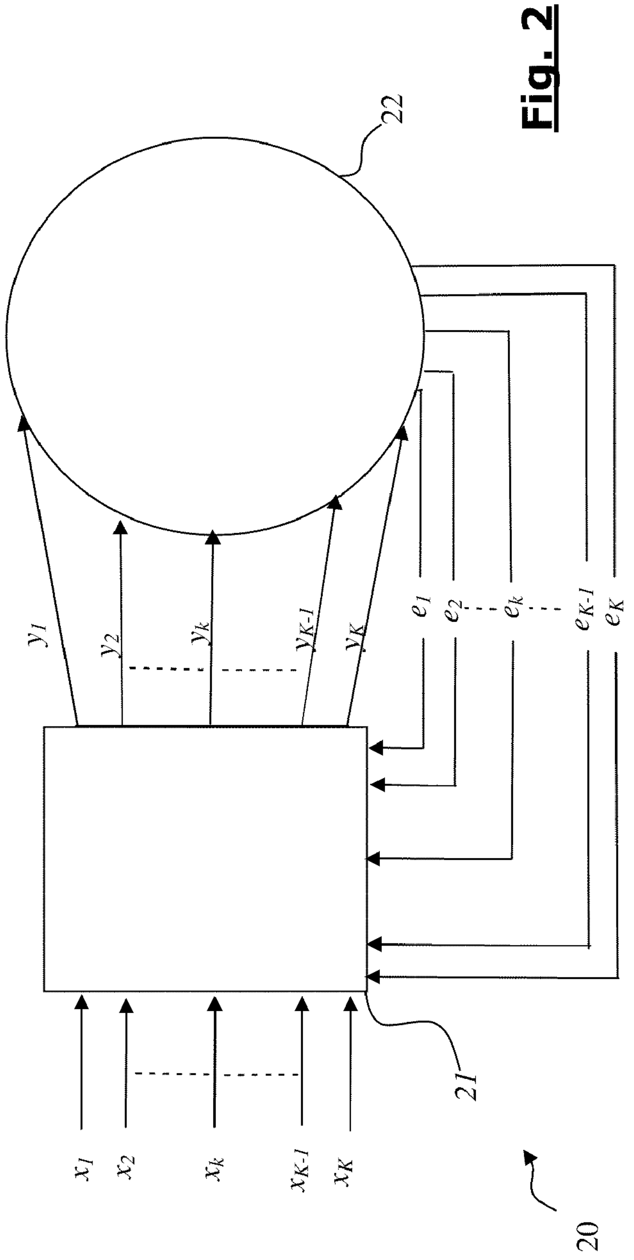
FIG. 2 is a diagrammatic representation of a configuration for the active reduction of a sound signal by means of a multi-route system according to the invention.

Thus, FIG. 2 represents a configuration 20 for the active reduction of noise disturbances by means of a multi-route system 21 according to the invention. This multi-route system 21 comprises:

- K noise microphones making it possible to measure K noise signals $x_k$,
- K monitoring microphones measuring K error signals $e_k$, and
- K transducers transmitting K counter-noise signals $y_k$ and producing an acoustic comfort bubble 22 larger than the comfort bubble 12, with k comprised between 1 and K. Of course, the number of monitoring microphones, the number of noise microphones and the number of transducers do not have to be equal. However, for a clearer description of the different operations carried out on each route of the multi-route system 21, we will assume here that the multi-route system 21 comprises the same number of monitoring microphones and transducers and one noise microphone.

Figure 3:
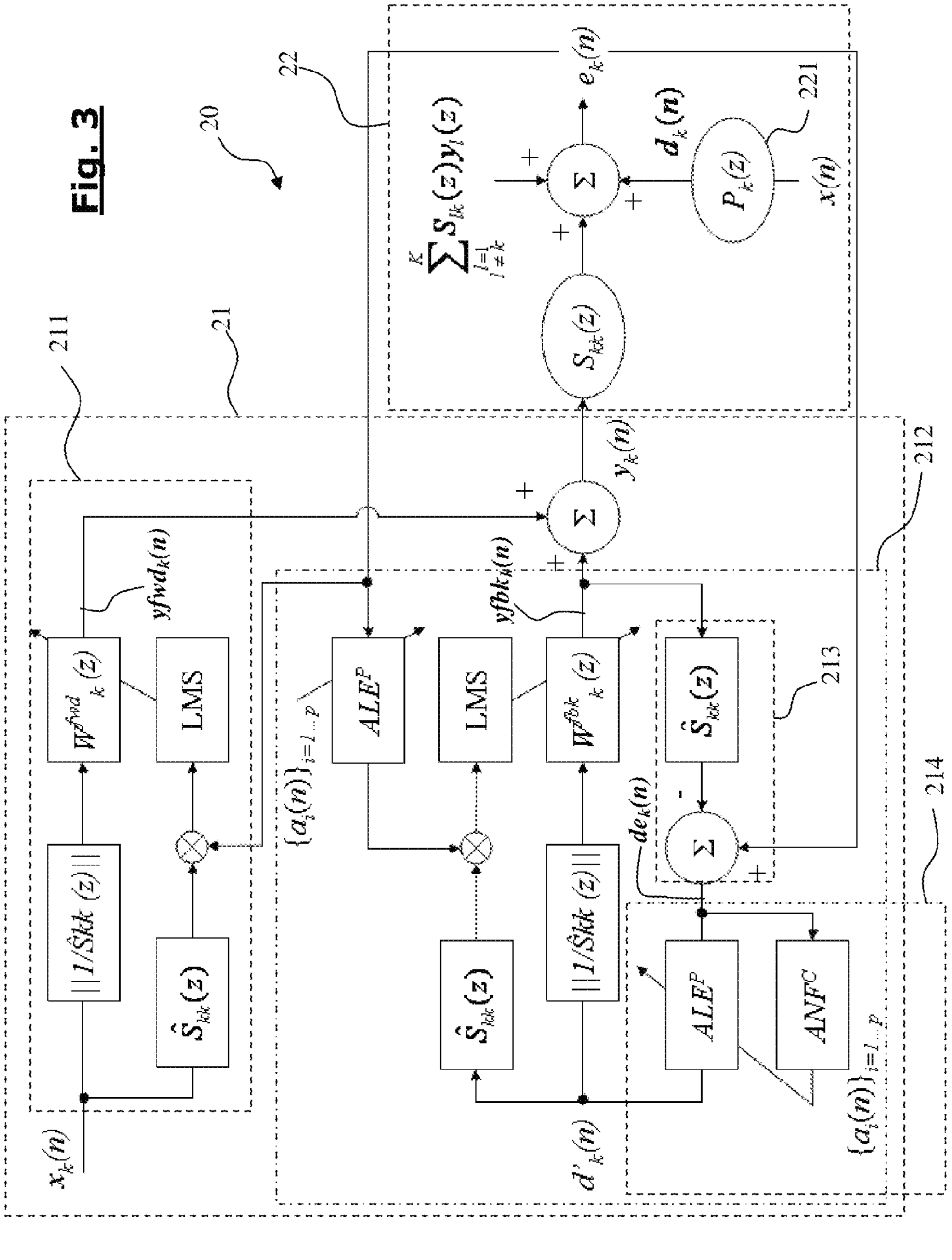
FIG. 3 is a diagrammatic representation in the form of functional blocks of the operations carried out on one route of a multi-route system according to the invention comprising a measurement of the noise signal with measurement microphones.

FIG. 3 is a representation in the form of block diagrams of a route k in the multi-route configuration 20 using the multi-route system 21 according to the invention making it possible to produce the comfort bubble 22. In FIG. 3, n denotes the discretized time, i.e. the sampling time, $S_{kk}$ the secondary path between the secondary source k and the monitoring microphone k, i.e. the direct acoustic path between the secondary source k and the microphone k. The module 221 $P_k$ represents the primary path between the microphone detecting the reference signal $x_k(n)$ and the monitoring microphone k. The monitoring microphone k makes it possible to measure the error signal $e_k$ in the comfort bubble. The operation of the system 21 in a route k will now be described.

The system 21 comprises two parts, namely a so-called feedforward part 211 and a so-called feedback part 212. The feedback part 212 comprises a finite impulsional response filter $W^{fbk}{}_k(Z)$, making it possible to generate and adjust a feedback counter-noise signal $yfbk_k(n)$. This feedback part 212 also comprises two filters FIR $\hat{S}_{kk}(z)$ digitally modelling the secondary path $S_{kk}$. A module 213, composed of a filter $\hat{S}_{kk}(z)$ and an adder Σ, makes it possible to carry out an estimation of the propagated noise signal $d_k(n)$ in the comfort bubble from the error signal $e_k(n)$ measured by the monitoring microphone k and the feedback counter-noise signal $yfbk_k(n)$ filtered by a filter $\hat{S}_{kk}(z)$. This module 213 provides at the output an estimated propagated noise signal $de_k(n)$. A detection and filtering module 214 makes it possible to carry out a detection of the periodic components of the propagated noise signal $d_k(n)$ from the analysis of the estimated propagated noise signal $de_k(n)$ and provides at the output a reference signal $d'_k(n)$ composed of the detected periodic components of the estimated propagated noise signal $de_k(n)$. This module 214 comprises a block $ANF^C$ detecting the periodic frequencies in the estimated propagated noise signal $de_k(n)$ and a block for $ALE^P$ (ALE standing for Adaptive Line Enhancer) band-pass filtering of the estimated propagated noise signal $de_k(n)$ at the frequencies of the periodic components detected by the detection block $ANF^C$. Details of this module 214 will be given later in the description. The reference signal $d'_k(n)$ is then used by a FIR filter $1/\hat{S}_{kk}(z)$ amplitude modelling the inverse of the modelled secondary path $\hat{S}_{kk}$ then by a filter $W^{fbk}{}_k(z)$ in order to adjust the feedback counter-noise signal $yfbk_k(n)$.

The coefficients of the filter $W^{fbk}{}_k(z)$ are adjusted by a minimization algorithm according to the least mean squares criterion, represented by the block LMS, as a function of the reference signal $d'_k(n)$ processed beforehand by a filter $\hat{S}_{kk}(z)$, and the error signal $e_k(n)$ that has undergone a band-pass filtering by a $ALE^P$ block at the frequencies of the periodic components detected in the estimated propagated noise signal $de_k(n)$.

The feedforward part 211 of the system 21 comprises a FIR filter $W^{fwd}{}_k(z)$ making it possible to generate and adjust a feedback counter-noise signal $yfwd_k(n)$ as a function of the noise signal $x_k(n)$ measured by measurement means and filtered beforehand by a FIR filter $1/\hat{S}_{kk}(Z)$ amplitude modelling the inverse of the modelled secondary path $\hat{S}_{kk}$. The coefficients of the filter $W^{fwd}{}_k(z)$ are adjusted by an LMS algorithm, represented by the block LMS as a function of, on the one hand, the error signal $e_k(n)$ and, on the other hand, the noise signal measured and processed beforehand by a filter $\hat{S}_{kk}(Z)$.

The feedforward $yfwd_k(n)$ and feedback $yfbk_k(n)$ counter-noise signals are then added by an adder Σ in order to obtain a counter-noise signal $y_k(n)$ which is transmitted to the comfort bubble by transmission means which are ultrasonic transducers in our example.

Thus, in the comfort bubble, the error signal $e_k(n)$ for the route k measured by a monitoring microphone (not shown) corresponds to the sum, on the one hand, of the propagated noise signal $d_k(n)$ and, on the other hand, of the counter-noise signals corresponding to each of the routes of the system 21 that have traveled the secondary paths $\hat{S}_{lk}(z)$ between the secondary sources associated with each of the routes and the monitoring microphone k, i.e.

$$\sum_{l=1}^{K} S_{lk}(z) y_l(n).$$

This can be written:

$$e_k(n) = \sum_{l=1}^{K} S_{lk}(z) y_l(n) + d_k(n).$$

It should be noted that, should the ultrasonic transducers be used as secondary sources, the error signal $e_k(n)$ for the route k measured by a monitoring microphone (not shown) this time corresponds to the sum, on the one hand, of the propagated noise signal $d_k(n)$ and, on the other hand, of the counter-noise signal $y_k(n)$ corresponding to the route k that has traveled the secondary path $S_{kk}(z)$, i.e. the acoustic path between the transducer k and the monitoring microphone k. In this case, $$e_k(n) = y_k(n) S_{kk}(n) + d_k(n).$$

Figure 4:
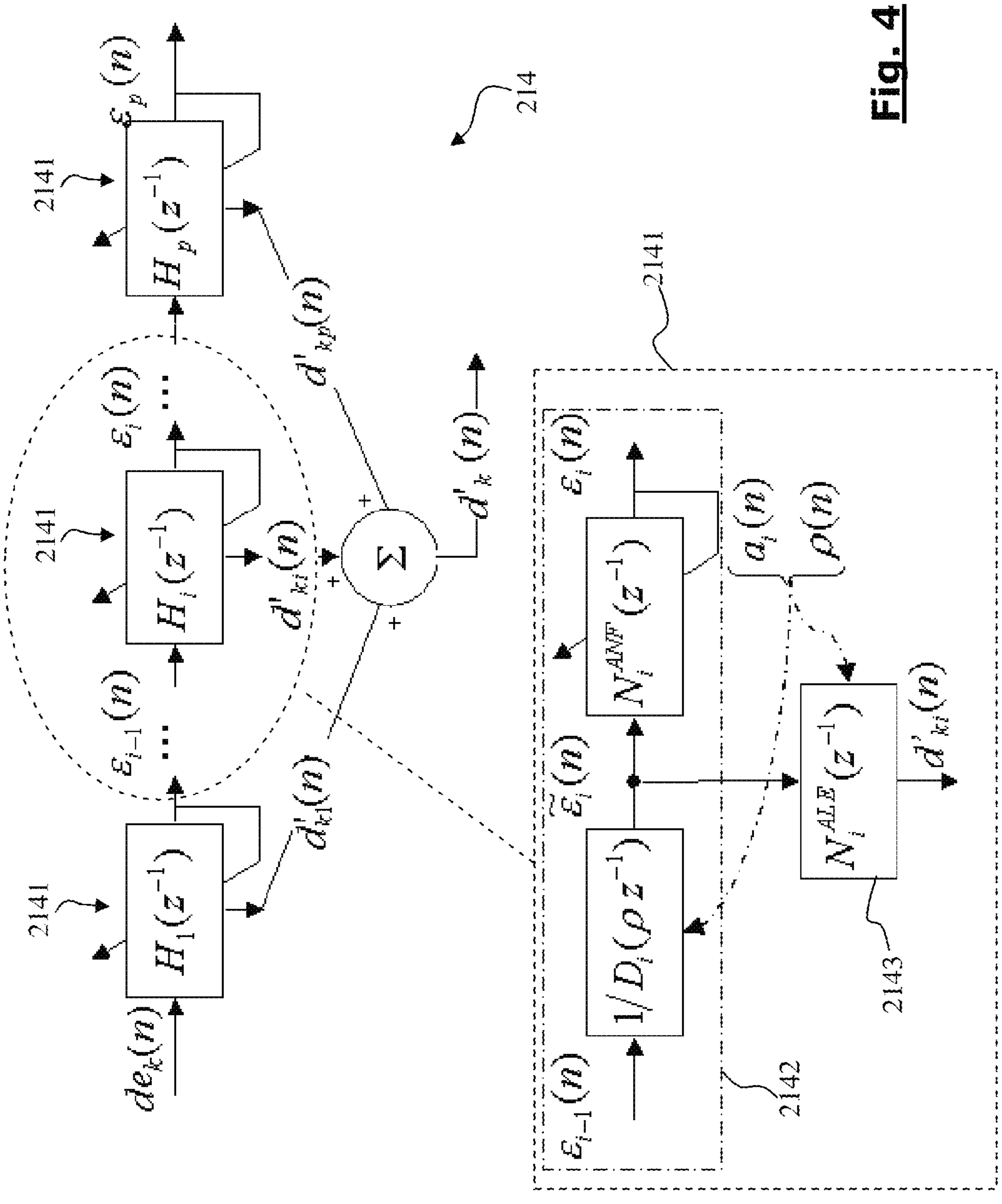
FIG. 4 is a diagrammatic representation in the form of functional blocks of a module for the detection and filtering of periodic components of a propagated noise signal on one route of a multi-route system according to the invention.

FIG. 4 is a block diagram representation of the module 214 detecting and filtering the periodic components of the estimated propagated noise signal $de_k(n)$. The frequency estimation method used in the present example involves an infinite impulsional response band-pass filtering of constant amplitude everywhere other than at the frequencies of the components of the noise signal, where the bandwidth is virtually zero. These filters are called "notch" filters and denoted ANF (Adaptive Notch Filter). Two types of notch filter exist, corresponding to two different approaches, namely the direct approach and the trellis approach. They are both in the rational form $H_i(z,\theta)=N_i(z,\theta)/D_i(z,\theta)$. For an input signal, the best set of coefficients θ is sought which minimize the quadratic error defined as the filtering of this input signal by the filter $H_i(z,\theta)$.

The trellis formulation is in the following form:

$$H_i(z) = \frac{1+\rho}{2} \frac{1 + a_i z^{-1} + z^{-2}}{1 + \frac{1+\rho}{2} a_i z^{-1} + \rho z^{-2}}$$

with the parameter $a_i$ linked directly to the frequency sought by the relationship $a_i=-2\cos(2\pi f_i)$ and ρ a strictly positive real number close to 1 called the contraction factor and recording the bandwidth around the cut frequency.

To optimize the arithmetic operations, and limit the disruptive impact of the detection and filtering module 214 on the system 21, a cascade decomposition, shown in FIG. 4, of this module 214 is chosen in order to determine the frequencies composing a given signal. Thus, for p periodic components, there are p filters $H_i(z)$ in series.

It should be noted that the cascade decomposition of the block 214 is indicated by a C, for cascade, in $ANF^C$ (see FIG. 3).

By setting out the following relationship:

$$\tilde{\varepsilon}_i(n) = \frac{1}{D_i} \varepsilon_{i-1}(n)$$

it is possible to determine each parameter $a_i$ by means of a skilful rewriting of the minimization algorithm according to the recursive least squares criterion (Recursive Least Squares (RLS) algorithm). To do this, use is made of the auto-correlation function recursively defined by:

$$\Phi_i(n) = \lambda\Phi_i(n-1) + \tilde{\epsilon}_i^2(n-1)$$

and, taking $\Theta(n)=[a_1(n) \ldots a_p(n)]^T$, $\Gamma(n)=[\Phi_1(n) \ldots \Phi_p(n)]^T$, $\tilde{E}(n)=[\tilde{\epsilon}_1(n-1) \ldots \tilde{\epsilon}_p(n-1)]^T$ and $E(n)=[\epsilon_1(n) \ldots \epsilon_p(n)]^T$, with T signifying transposed, the following recurrence relation is used:

$$\Theta(n) = \Theta(n-1) + \Gamma^{-1}(n)\tilde{E}(n)E(n).$$

Finally, λ and ρ are adapted exponentially by means of the following recursion:

$$\begin{cases} \lambda(n) = \lambda_0\lambda(n-1) + (1-\lambda_0)\lambda_\infty \\ \rho(n) = \rho_0\rho(n-1) + (1-\rho_0)\rho_\infty \end{cases}$$

which makes it possible to start with a high bandwidth, so as to allow each section 2141 to detect a periodic component, then narrow it in order to be able to make this detection more precise. It is thus a means of limiting the conflicts between sections, knowing that the latter can arise regardless.

For questions of stability and rapidity of convergence, the reference signal $d'_k(n)$ and the error signal $e_k(n)$ are filtered by band-pass filters centred around the frequencies present in the estimated propagated noise signal $de_k(n)$. The complementary of a notch filter, whatever its formulation, is a band-pass filter, denoted $N^{ALE}(z^{-1})$, in which the central filtering frequency is involved part.

Thus, as shown in FIG. 4, the detection and filtering module 112 is composed of as many sections 2141 in cascade as there are periodic components to be detected. Each section i is in the form of a filter $H_i(z^{-1})$ comprising:

- an assembly 2142, composed of two blocks denoted $1/D_i(\rho z^{-1})$ and $N_i^{ANF}(z^{-1})$. This assembly 2142 is provided to carry out the detection of a periodic component $a_i$ of the estimated propagated noise signal $de_k(n)$; and
- a filter 2143, denoted $N_i^{ALE}(z^{-1})$, and provided to filter the estimated propagated noise signal $de_k(n)$ at the frequency of the periodic component $a_i$ detected by the assembly 2142. This filter 2143 provides at the output a signal $d'_{ki}(n)$ composed solely of the periodic component $a_i$ of the estimated propagated noise signal $de_k(n)$.

The reference signal $d'_k(n)$ is obtained by adding all the signals $d'_{ki}(n)$ provided by the filters $N_i^{ALE}(z^{-1})$ of the sections 2141.

It should be noted that this addition operation is indicated by a P, for parallel, in $ALE^P$ (see FIG. 3).

The operations of noise signal analysis, generation and adjustment of the counter-noise signals $y_k(n)$ for all the routes k of the multi-route noise disturbance reduction system 21 according to the invention can be integrated on a single circuit board.

Figure 5:
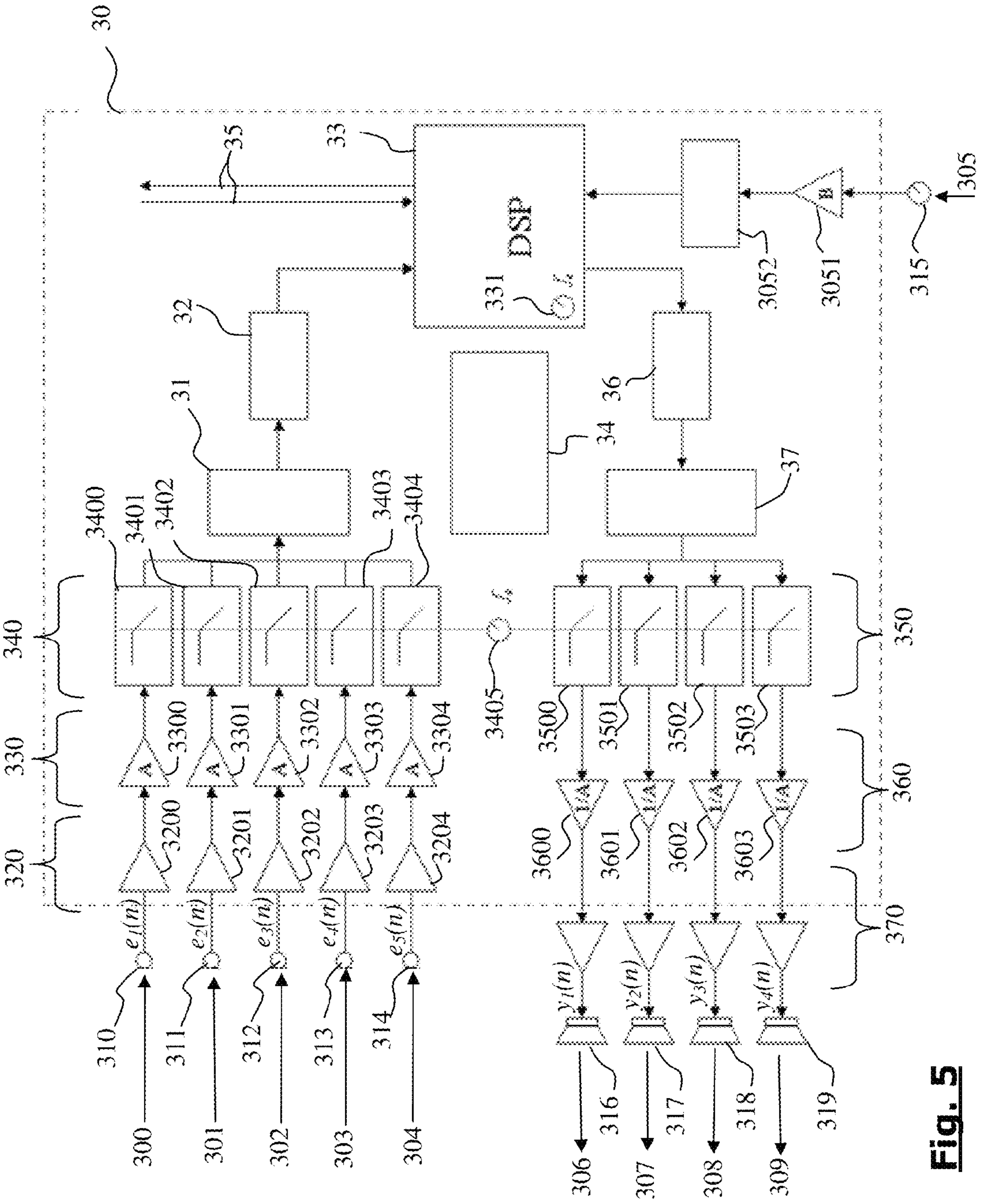
FIG. 5 is a diagrammatic representation of a multi-route circuit board utilized in the multi-route system according to the invention.

FIG. 5 diagrammatically represents an example of a circuit board 30 for a multi-route noise disturbances reduction system having 6 input routes 300-305, and 4 output routes 306-309. At the input of this board 30:

- the routes 300-303 corresponding to four error signals, respectively $e_1(n)$-$e_4(n)$, measured by four monitoring microphones, respectively 310-313, are arranged in the comfort bubble 22;
- the route 304 corresponds to the noise signal x(n) measured by a noise microphone; and

- the route 305 corresponds to a signal from a potentiometer 315 making it possible to adjust the feedback and feedforward convergence coefficients involved in the LMS algorithms used.

At the output of this board 30:

- the routes 306-309 correspond to four counter-noise signals, respectively $y_1(n)$-$y_4(n)$, intended to be transmitted by four transducers, respectively 316-319, appropriately arranged.

For each of the routes 300-304, the board comprises:

- a pre-amplification step 320, carrying out a pre-amplification of the signals of each of the routes 300-304, using pre-amplifiers 3200-3204;
- a gain step 330, arranged at the output of the step 320, and applying a gain to the signals of each of the routes 300-304 using adjustable gain amplifiers 3300-3304;
- a step 340 of antialiasing filtering at the output of the gain step 330, and carrying out antialiasing filtering of the signals of each of the routes 300-304, using antialiasing filters 3400-3404. The sampling frequency at the filters 3400-3404 can be adjusted using a module 3405;
- at the output of the step 340, a multiplexer 31 carrying out multiplexing of the signals of the routes 300-304; and
- at the output of the multiplexer 31, an analogue-digital converter 32, carrying out an analogue-digital conversion of the multiplexed signal.

The multiplexed digital signal, obtained at the output of the converter 32, then enters a DSP-type processor 33 which makes it possible to carry out for each route the operations described above and represented diagrammatically in FIGS. 3 and 4. The processor 33 used in the present example is an industrial-finish Analogue Devices processor from the SHARC range, one therefore resistant to extreme temperatures. The code is implemented via the interface developed by Analogue Devices i.e. the VisualDSP++ software, which possesses a high-level C compiler. It is possible to work either in floating point or in fixed point. The frequency of sampling in the processor is parameterizable, using a module 331, to suit all cases of active reduction of the energy of a sound signal.

The DSP 33 was dimensioned to support operations inherent in the LMS algorithms used. The DSP can support more complex algorithms than those used because an external memory 34 is present on the board 30, in order to meet any additional memory and calculation costs.

In the case of a multi-board system, the different boards can be linked using the connection lines 35. This eventuality was considered in order to be able to infinitely extend the applications of active noise disturbances reduction applications and not to have limitations due to the processor 33.

At the output of the processor 33, the digital signal is composed of the counter-noise signals $y_1(n)$-$y_4(n)$. This digital signal is converted using a digital-analogue converter 36. Then the analogue signal obtained enters a demultiplexer 37 and undergoes a demultiplexing. After the demultiplexing the different counter-noise signals $y_1(n)$-$y_4(n)$ are separated and are situated on the output routes 306-309. Before being transmitted by the transducers 316-319, the counter-noise signals undergo:

- a smoothing by a smoothing step 350 comprising low-pass filters 3500-3503. The frequency of sampling at the filters 3500-3503 can be adjusted using the module 3405;
- a gain reduction by a gain step 360 comprising adjustable gain amplifiers 3600-3603; and
- a power amplification by a power amplification step 370 comprising power amplifiers. This power amplification step 370 does not have to be located on the board 30 as shown in FIG. 5.

The feedback and feedforward convergence coefficients adjustment signal from the potentiometer 315 on the route 305 undergoes an amplification by means of an amplifier 3051 then an analogue-digital conversion by means of an analogue-digital converter 3052 before entering the processor 33. This convergence coefficient is a strictly positive weighting factor, less than 1, applied at the updating in the LMS algorithm of the coefficients of the various filters mentioned above.

Figure 6:
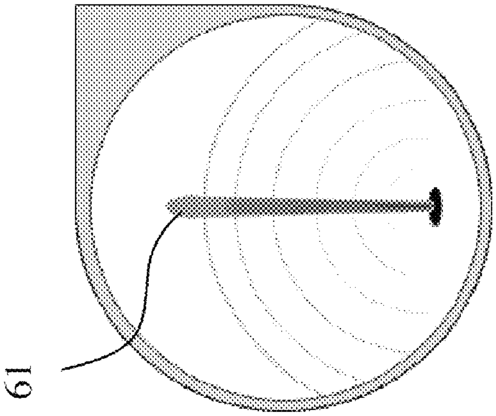
FIG. 6 is a representation of a transmission beam of an ultrasonic transducer used in the system according to the invention.

The transducers 316-319 used in the present example are ultrasonic transducers. These ultrasonic transducers 316-319 have a very reduced transmission beam 61, shown in FIG. 6. Furthermore, the ultrasounds, completely inaudible on transmission, distort as they are propagated in the air and shift into the audible spectrum and the volume at which they become audible is completely predictable.

Figure 7:
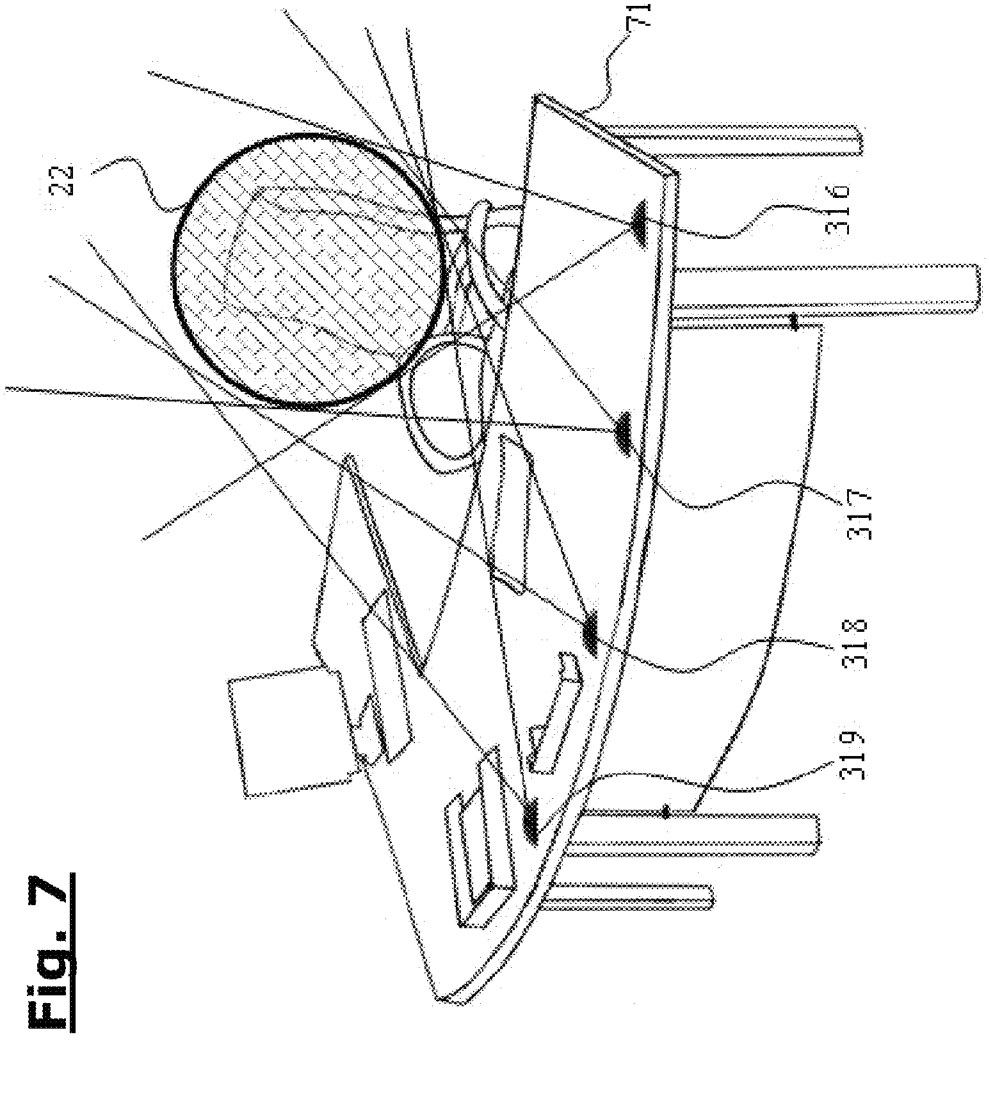
FIG. 7 is a first embodiment example of the multi-route system according to the invention for obtaining a comfort bubble.

FIG. 7 diagrammatically represents a first embodiment example of the multi-route system according to the invention for obtaining a comfort bubble 22 using the 4 ultrasonic transducers 316-319 appropriately placed on an office desk 71. The positioning of these transducers is clearly not limited solely to an office. They can perfectly well be arranged around an opening, a window or a door for example. The comfort bubble 22 obtained is situated on the office desk 71 substantially at a level corresponding to the level of a user's head.

Figure 8:
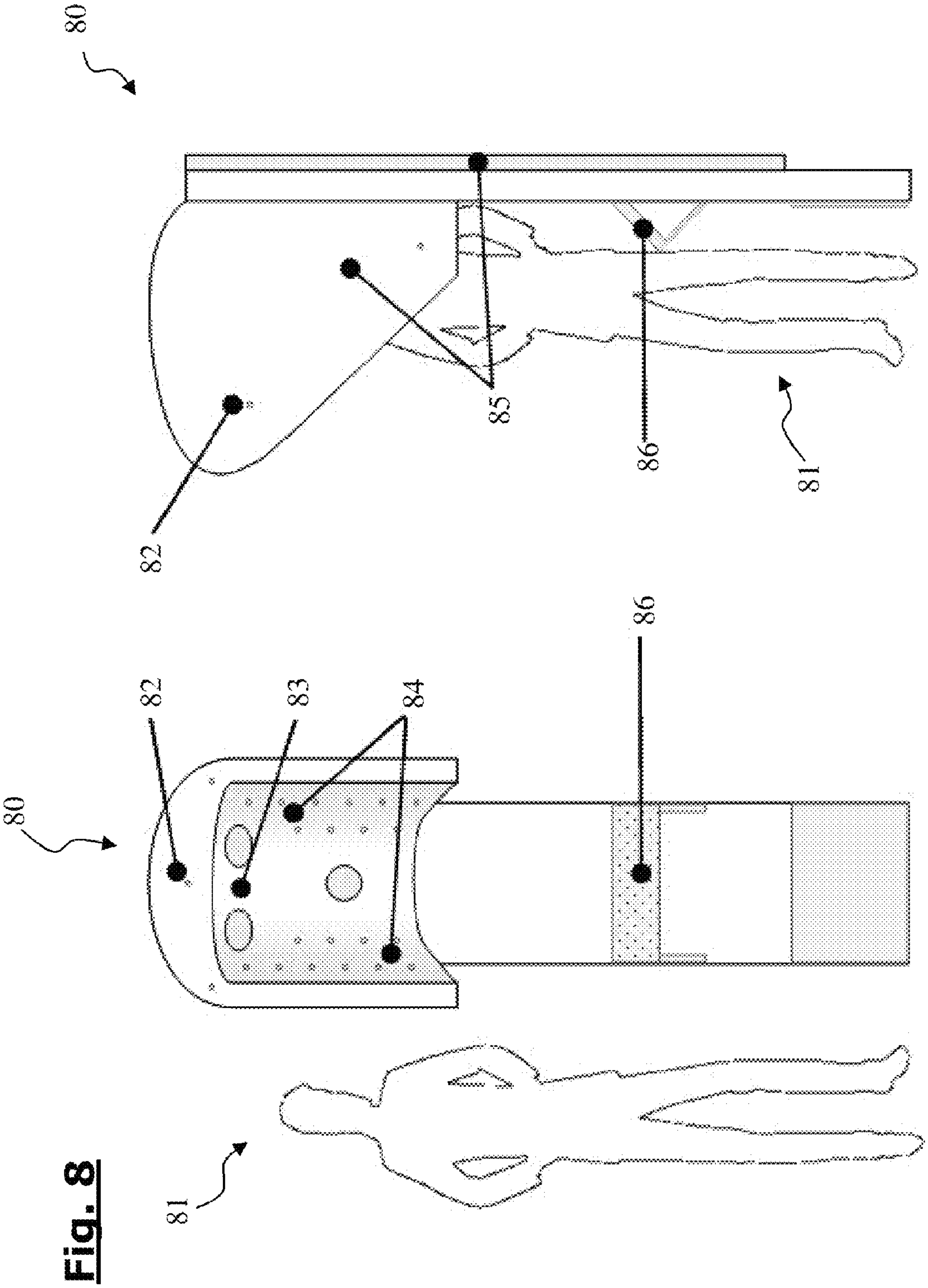
FIG. 8 a second embodiment example of the multi-route system according to the invention for obtaining a comfort bubble.

Another embodiment of the system according to the invention is diagrammatically represented in FIG. 8. It is a cubicle 80 intended to accommodate one or more users 81 in order to provide them with a noise disturbances reduction zone around their heads. It is designed to be installed in public spaces and in factories, and can also constitute an advertising support.

The principle is the following: a large number of noise microphones 82 installed in the structure of the cubicle 81 supply the noise signals, bases for the algorithm described previously for calculating the counter-noise signals propagated by a large number of secondary sources 83 installed in the cubicle 80. A network of monitoring microphones 84, around which the comfort bubble is situated, allows the adaptation in real time of the filters described above. Display panels 85 allow the display of information such as advertisements. The cubicle 80 comprises one or more seats or rests 86 allowing the user 81 to sit.

The advantage of such an integration of the comfort bubble is that the low-frequency performances of the active control are combined with the known effectiveness of acoustic processing by passive materials with which the structure and cabin of the cubicle are lined. Thus, a completely satisfactory and homogeneous attenuation is achieved over the whole noise spectrum.

The invention is, of course, not limited to the examples of applications which have just been described and can be applied to the reduction of the energy of any sound signal in a determined zone.

The invention claimed is:

1. Method for the active reduction in a determined zone (22) of the energy of a sound signal ($d_k(n)$), called propagated noise signal, generated in said zone (22) by a primary signal ($x_k(n)$), called noise signal, said method comprising a transmission, by transmission means, of at least one counter-noise signal ($y_k(n)$) comprising at least one first so-called feedback counter-noise signal ($yfbk_k(n)$), counteracting said propagated noise signal ($d_k(n)$), said method also comprising at least one iteration of the following operations:

- measurement, by measurement means arranged in said determined zone (22), of a so-called error signal ($e_k(n)$), representing information on the effectiveness of the reduction of the energy of the propagated noise signal ($d_k(n)$) in said zone (22);

modelling, by at least one first filter ($\hat{S}_{kk}(z)$), of a direct acoustic path ($S_{kk}$), called secondary path, between said transmission means of the counter-noise signal ($y_k(n)$) and said measurement means of said error signal ($e_k(n)$);

detection of at least one periodic component of said propagated noise signal ($d_k(n)$) by analysis of a propagated noise signal ($de_k(n)$) estimated from, on the one hand, the error signal ($e_k(n)$) and, on the other hand, the feedback counter-noise signal ($yfbk_k(n)$) processed by the first filter ($\hat{S}_{kk}(z)$), said detection providing said periodic component; and adjustment of said feedback counter-noise signal ($yfbk_k(n)$) as a function of said detected periodic component, of said error signal ($e_k(n)$) and of said modelled secondary path ($\hat{S}_{kk}(z)$).

2. Method according to claim 1, characterized in that it also comprises a band-pass filtering of the estimated propagated noise signal ($de_k(n)$), at the frequency of all or some of the detected periodic components, said filtering providing a so-called reference signal ($d'_k(n)$).

3. Method according to claim 2, characterized in that the adjustment of the feedback counter-noise signal ($yfbk_k(n)$) comprises an adjustment of at least one coefficient of a second, finite impulsional response filter ($W^{fbk}{}_k(z)$), said second filter being provided to adjust said feedback counter-noise signal ($yfbk_k(n)$) as a function of the reference signal ($d'_k(n)$) filtered by a third, finite impulsional response, filter ($1/\hat{S}_{kk}(z)$) amplitude modelling the inverse of the secondary path.

4. Method according to claim 3, characterized in that at least one coefficient of the second filter ($W^{fbk}{}_k(z)$) is adjusted by an algorithm of the minimization algorithm type according to the least mean squares (LMS) criterion as a function of the reference signal (d'k(n)) processed beforehand by the first filter ($\hat{S}_{kk}(z)$), of the error signal ($e_k(n)$) that has previously undergone a band-pass filtering at the frequency of all or some of the detected periodic components and of a so-called feedback convergence coefficient.

5. Method according to claim 1, characterized in that the counter-noise signal ($y_k(n)$) also comprises a so-called feedforward counter-noise signal ($yfwd_k(n)$), adjusted as a function of the error signal ($e_k(n)$), of the noise signal ($x_k(n)$) measured by measurement means (314).

6. Method according to claim 5, characterized in that it also comprises an amplitude modelling of the inverse of the secondary path ($S_{kk}$) by at least one fourth, finite impulsional response, filter ($1/S_{kk}(z)$).

7. Method according to claim 6, characterized in that the adjustment of the feedforward counter-noise signal ($yfwd_k(n)$) comprises an adjustment of at least one coefficient of a fifth, finite impulsional response, filter ($W^{fwd}{}_k(z)$), said fifth filter being provided to adjust said feedforward counter-noise signal ($yfwd_k(n)$) as a function of the noise signal ($x_k(n)$) processed beforehand by the fourth filter ($1/\hat{S}_{kk}(z)$).

8. Method according to claim 7, characterized in that at least one coefficient of the fifth filter ($W^{fwd}{}_k(z)$) is adjusted by an algorithm of the least mean squares (LMS) algorithm type as a function of the error signal ($e_k(n)$), of the measured noise signal ($x_k(n)$) processed beforehand by a sixth filter ($\hat{S}_{kk}(z)$) modelling the secondary path ($S_{kk}$) and of a so-called feedforward convergence coefficient.

9. Method according to claim 1, characterized in that it is used to attenuate at least one propagated noise signal ($d_k(n)$) by transmission of a plurality of counter-noise signals ($y_1(n)$-$y_4(n)$) by a plurality of transmission means (316-319).

10. System of active reduction, in a determined zone (22), of the energy of a sound signal ($d_k(n)$), called propagated noise signal, generated in said zone (22) by a primary signal ($x_k(n)$), called noise signal, by transmission of at least one counter-noise signal ($y_k(n)$) comprising at least one first so-called feedback counter-noise signal ($yfbk_k(n)$), counteracting said propagated noise signal ($d_k(n)$) in the determined zone (22), said system comprising:

means (316-319) for transmitting the counter-noise signal ($y_k(n)$);

means (310-313) of measuring, in said determined zone (22), a so-called error signal ($e_k(n)$), representing information on the effectiveness of the reduction of the energy of said propagated noise signal ($d_k(n)$);

at least one first filter ($\hat{S}_{kk}(z)$) for modelling a direct acoustic path ($S_{kk}$), called secondary path, between said transmission means (316-319) of the counter-noise signal ($y_k(n)$) and said measurement means (310-313) of said error signal ($e_k(n)$), means (213) for estimating the propagated noise signal ($d_k(n)$) from, on the one hand, the error signal ($e_k(n)$) and, on the other hand, the feedback counter-noise signal ($yfbk_k(n)$) processed by the first filter ($\hat{S}_{kk}(z)$), said means (213) providing an estimated propagated noise signal ($de_k(n)$), means (214) for detecting and providing at least one periodic component of said propagated noise signal ($d_k(n)$) by analysis of said estimated propagated noise signal ($de_k(n)$); and means for adjusting said feedback counter-noise signal ($yfbk_k(n)$) as a function of said detected periodic component, of said error signal ($e_k(n)$) and of said modelled secondary path ($\hat{S}_{kk}(z)$).

11. System according to claim 10, characterized in that the means (316-319) for transmitting the counter-noise signal ($y_k(n)$) comprise ultrasonic transducers having a reduced transmission beam (61).

12. System according to claim 10, characterized in that it also comprises means for band-pass filtering (214) of the estimated propagated noise signal ($de_k(n)$) at the frequency of all or some of the detected periodic components, said filtering means providing a reference signal ($d'_k(n)$).

13. System according to claim 12, characterized in that the means for adjusting the feedback counter-noise signal ($yfbk_k(n)$) comprise at least one second, finite impulsional response, filter ($W^{fbk}{}_k(z)$) provided to adjust said feedback counter-noise signal ($yfbk_k(n)$) as a function of the reference signal ($d'_k(n)$) filtered by a third filter ($1/\hat{S}_{kk}(z)$) amplitude modelling the inverse of the second path.

14. System according to claim 10, characterized in that the counter-noise signal ($y_k(n)$) comprises a second so-called feedforward counter-noise signal ($yfwd_k(n)$), the system also comprising means for adjusting said feedforward counter-noise signal ($yfwd_k(n)$) as a function of the error signal ($e_k(n)$) and of the noise signal ($x_k(n)$).

15. System according to claim 14, characterized in that it also comprises a fourth, finite impulsional response, filter ($1/\hat{S}_{kk}(z)$), arranged for amplitude modelling the inverse of the secondary path.

16. System according to claim 15, characterized in that it also comprises a fifth filter ($W^{fwd}{}_k(z)$), provided to adjust the feedforward counter-noise signal ($yfwd_k(n)$), as a function of the noise signal ($x_k(n)$) processed by the fourth filter ($1/\hat{S}_{kk}(z)$).

17. System according to claim 10, characterized in that it also comprises a plurality of transmission means (316-319) of a plurality of counter-noise signals ($y_1(n)$-$y_4(n)$).

* * * * *

UNITED STATES PATENT AND TRADEMARK OFFICE

CERTIFICATE OF CORRECTION

PATENT NO. : 8,401,204 B2
APPLICATION NO. : 12/530506
DATED : March 19, 2013
INVENTOR(S) : Odent et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 862 days.

Signed and Sealed this
First Day of September, 2015

Michelle K. Lee
*Director of the United States Patent and Trademark Office*